United States Patent
Lee et al.

(10) Patent No.: US 7,707,471 B2
(45) Date of Patent: Apr. 27, 2010

(54) METHOD OF DEFINING FAULT PATTERN OF EQUIPMENT AND METHOD OF MONITORING EQUIPMENT USING THE SAME

(75) Inventors: Young-Hak Lee, Suwon-si (KR); Tae-Jin Yun, Suwon-si (KR); Won-Soo Choi, Seongnam-si (KR); Mun-Hee Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 417 days.

(21) Appl. No.: 11/892,090

(22) Filed: Aug. 20, 2007

(65) Prior Publication Data
US 2008/0059856 A1 Mar. 6, 2008

(30) Foreign Application Priority Data
Aug. 29, 2006 (KR) .................. 10-2006-0082373

(51) Int. Cl.
*G01R 31/28* (2006.01)
*G06F 7/02* (2006.01)

(52) U.S. Cl. .................. 714/728; 714/736; 714/738; 714/819

(58) Field of Classification Search .................. None
See application file for complete search history.

(56) References Cited

U.S. PATENT DOCUMENTS 6,457,140 B1 * 9/2002 Lindberg et al. ............ 714/6
7,480,205 B2 * 1/2009 Wei ............................. 367/37
7,587,651 B2 * 9/2009 Kuo et al. .................... 714/745

FOREIGN PATENT DOCUMENTS

| JP | 10-093865 | 4/1998 |
| JP | 2001-156141 | 6/2001 |
| JP | 2002-093865 | 3/2002 |
| KR | 10-0200480 | 3/1999 |
| KR | 1020000028114 A | 5/2000 |
| KR | 1020010009841 A | 2/2001 |
| KR | 10-2005-0117818 | 12/2005 |

OTHER PUBLICATIONS

Decision of Grant and Prior Arts issued Sep. 19, 2007 for corresponding Korean Patent Application No. 10-2006-0082373.

* cited by examiner

*Primary Examiner*—Christine T Tu
(74) *Attorney, Agent, or Firm*—Harness, Dickey & Pierce

(57) ABSTRACT

Provided is a method of forming reference information for defining a fault pattern of equipment, and monitoring equipment. One example embodiment method may include performing an angle spectrum analysis by re-classifying fault points distributed on a plane, the plane including a first component axis and a second component axis, and the re-classifying fault points including calculating an angle for each of the fault points with reference to any one of the first component axis and the second component axis of the plane, and forming a reference fault pattern for defining a fault pattern of the re-classified fault points.

20 Claims, 6 Drawing Sheets

FIG. 1
(CONVENTIONAL)
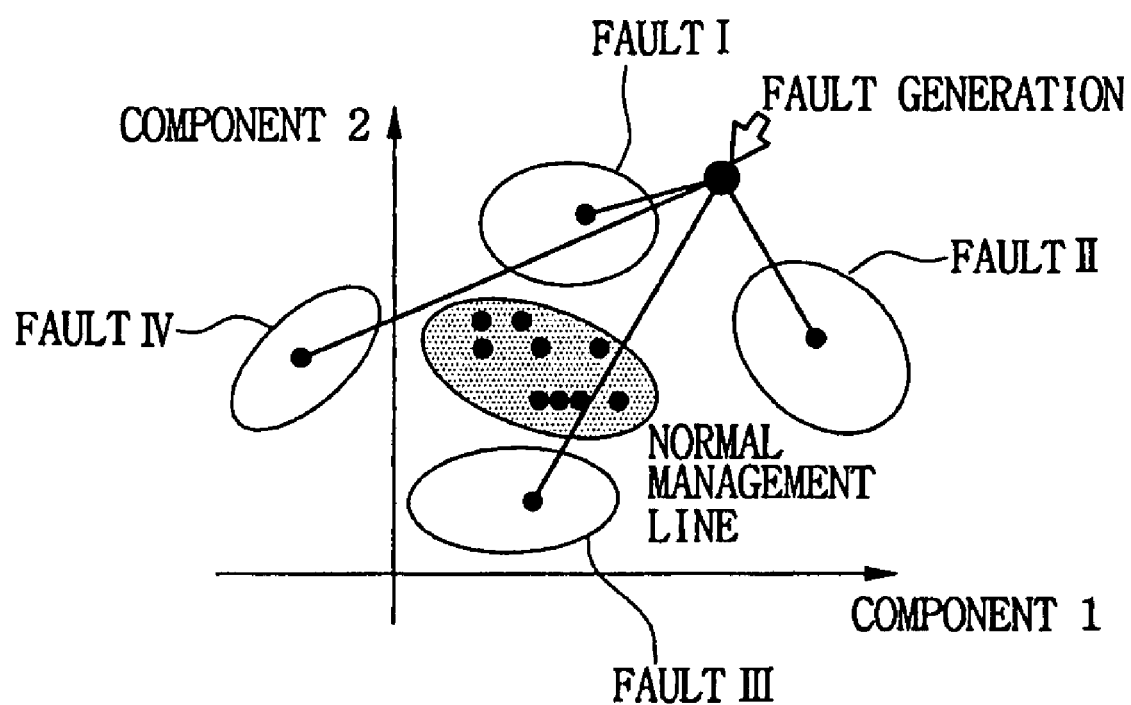

| FAULT No. | FAULT RECOGNITION INFORMATION | STANDARD FAULT PATTERN | FAULT CHARACTERISTICS | DEGREE OF DANGER | TREATMENT | FREQUENCY |
|---|---|---|---|---|---|---|
| I | | | | | | |
| II | | | | | | |
| III | | | | | | |
| IV | | | | | | |

METHOD OF DEFINING FAULT PATTERN OF EQUIPMENT AND METHOD OF MONITORING EQUIPMENT USING THE SAME

PRIORITY CLAIM

A claim of priority is made to Korean Patent Application No. 10-2006-0082373, filed on Aug. 29, 2006, the disclosure of which is hereby incorporated herein by reference in its entirety.

BACKGROUND

1. Field

Example embodiments of the present invention may relate to a method of monitoring equipment and, more particularly, to a method of forming standard information for defining a fault pattern of semiconductor manufacturing equipment and a method of monitoring semiconductor manufacturing equipment using the same.

2. Description of Related Art

Generally, a semiconductor device is manufactured by repeatedly and selectively performing a plurality of processes such as diffusion, deposition, exposure, etching, cleaning, etc. on a wafer. Semiconductor manufacturing equipment is used to perform each process.

The semiconductor manufacturing equipment for performing each process may generate a fault (e.g., error) while performing the process. Throughout the specification the term "fault" may be interchangeably used with "error." When a fault is detected, the equipment may transmit fault data to a controller, which may display the fault state or the controller may generate an alarm. Accordingly, an operator may be notified of the fault and may correct the fault.

In a conventional fault monitoring method, faults generally detected by the monitoring method are divided into a plurality of fault groups, each of which has similar fault states.

The conventional monitoring method includes two steps, e.g., (1) a process of extracting fault patterns due to faults and storing the extracted fault pattern in a database, and (2) a process of recognizing the fault pattern.

FIG. 1 is a graph illustrating a conventional method of determining a fault pattern.

Referring to FIG. 1, FAULTS I to IV are fault pattern regions extracted in an offline state and distributed on a plane. Here, "plane" may mean a 2-D graphical representation. These fault regions are formed on the basis of received fault data from previously operated semiconductor manufacturing equipment. The fault pattern region information may be stored in a database.

The fault pattern generated by semiconductor manufacturing equipment may be recognized as follows. As shown in FIG. 1, when received (detected) data deviates from a normal management region, an operator determines whether the detected data is similar to fault pattern regions I to IV stored in the database. The similarity is determined based on a statistical distance between the received data and the fault pattern regions I to IV. Therefore, as the statistical distance increases between the received data and the fault pattern regions I to IV, similarity between the received data and the fault pattern region I to IV decreases.

However, when the received data is within any one boundary of the fault pattern regions I to IV, the operator determines that the fault of the received data corresponds to that fault pattern region. When the received data is not within any boundary of the fault pattern regions I to IV, the operator determines that a new fault may have been generated. At this point, the operator may take the semiconductor manufacturing equipment offline, and input a pattern for the new fault to the database. In the conventional monitoring method, because the new fault pattern is determined based on the statistical distance, there is a transition time for determining the new fault pattern.

In addition, determining whether any data received (detected) from the semiconductor manufacturing equipment is accurately included in any one of the fault pattern regions I to IV is difficult. Also, the determination through the proximity of the statistical distance may cause inaccurate definition of the fault pattern of the received data. Therefore, an operator who receives inaccurate defined fault patterns may perform the wrong correction on the semiconductor manufacturing equipment. For example, if a fault is incorrectly determined to have been caused by heat, increasing/decreasing the heat may cause further damage to a semiconductor device when the fault was really caused by lack of oxygen.

SUMMARY

Example embodiments of the present invention may be directed to a method of forming reference information for defining a fault pattern of equipment and monitoring equipment using the same. The method may include performing an angle spectrum analysis by re-classifying fault points distributed on a plane, the plane including a first component axis and a second component axis, and the re-classifying fault points including calculating an angle for each of the fault points with reference to any one of the first component axis and the second component axis of the plane, and forming a reference fault pattern for defining a fault pattern of the re-classified fault points.

In an example embodiment of the present invention, a method may include determining a fault pattern for a first set fault points generated by monitored equipment, by performing a first angle spectrum analysis by re-classifying the first set of fault points distributed on a plane, the plane including a first component axis and a second component axis, and the re-classifying of the first set of fault points including calculating an angle for each of the first set of fault points with reference to any one of the first component axis and the second component axis of the plane, determining whether the monitored equipment fault pattern matches a reference fault pattern, and transmitting results of the determination.

In another example embodiment of the present invention a method of monitoring equipment may include performing a first angle spectrum analysis on a first set of fault points generated by an equipment, determining a standard fault pattern for the first set fault points by determining contributions of variables to the first set of fault points, storing the standard fault pattern to a database, performing a second angle spectrum analysis of a second set of fault points generated by the monitored equipment, determining a fault pattern for the second set fault points generated by determining contributions of variables to the first set of fault points, and determining whether the monitored equipment fault pattern matches a stored standard information. The method may further include displaying at least one of treatment information if the monitored equipment fault pattern matches the stored standard information and variables affecting the fault pattern if the monitored equipment fault pattern does not match the standard information.

BRIEF DESCRIPTION OF THE DRAWINGS

The foregoing and other aspects of example embodiments of the present invention may be apparent from the detail descriptions thereof and as illustrated in the accompanying drawings. The drawings are not necessarily to scale, emphasis instead being placed upon illustrating the principles of example embodiments.

FIG. 1 is a graph illustrating a conventional method of determining fault patterns;

DETAILED DESCRIPTION OF EXAMPLE EMBODIMENTS

Figure 2:
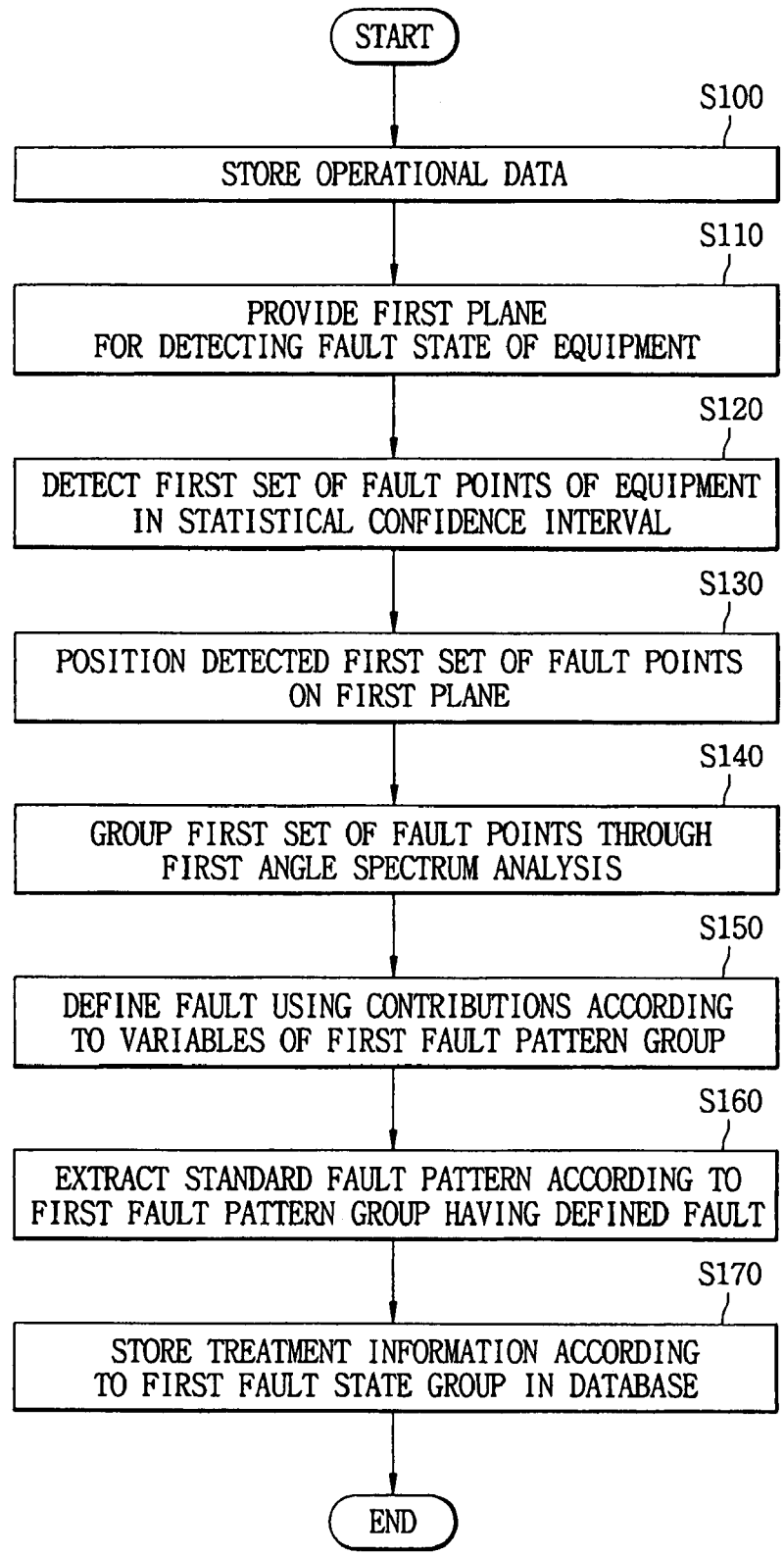
FIG. 2 is a flow chart illustrating a method of forming standard information to define a fault pattern in accordance with an example embodiment of the present invention.

Example embodiments of the present invention will now be described more fully hereinafter with reference to the accompanying drawings.

It will be understood that when an element or layer is referred to as being "on", "connected to" or "coupled to" another element or layer, it may be directly on, connected or coupled to the other element or layer or intervening elements or layers may be present. In contrast, when an element is referred to as being "directly on," "directly connected to" or "directly coupled to" another element or layer, there may be no intervening elements or layers present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms may be only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting. As used herein, the singular forms "a", "an" and "the" may be intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-section illustrations that may be schematic illustrations of idealized embodiments (and intermediate structures). As such, variations from the shapes of the illustrations as a result, for example, of manufacturing techniques and/or tolerances, are to be expected. Thus, the example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the drawings are schematic in nature and their shapes are not intended to illustrate the actual shape of a region of a device and are not intended to limit the example embodiments.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Since a method of forming standard information in accordance with the present invention is included in a fault pattern recognition method, detailed description of the standard information forming method is also included in the description of the fault pattern recognition method.

Figure 3:
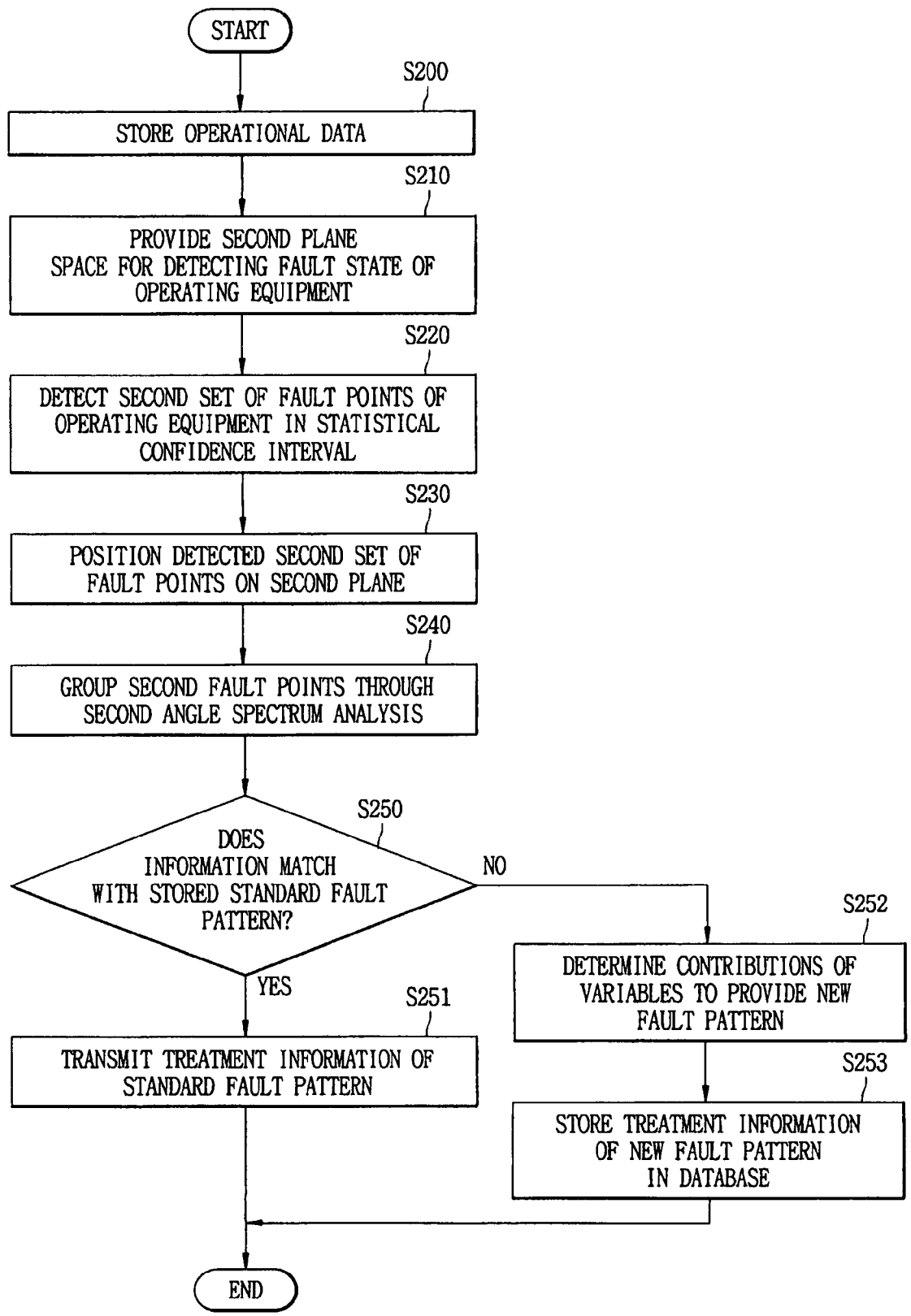
FIG. 3 is a flow chart illustrating a method of determining a fault pattern of semiconductor manufacturing equipment in accordance with an example embodiment of the present invention.
Figure 4:
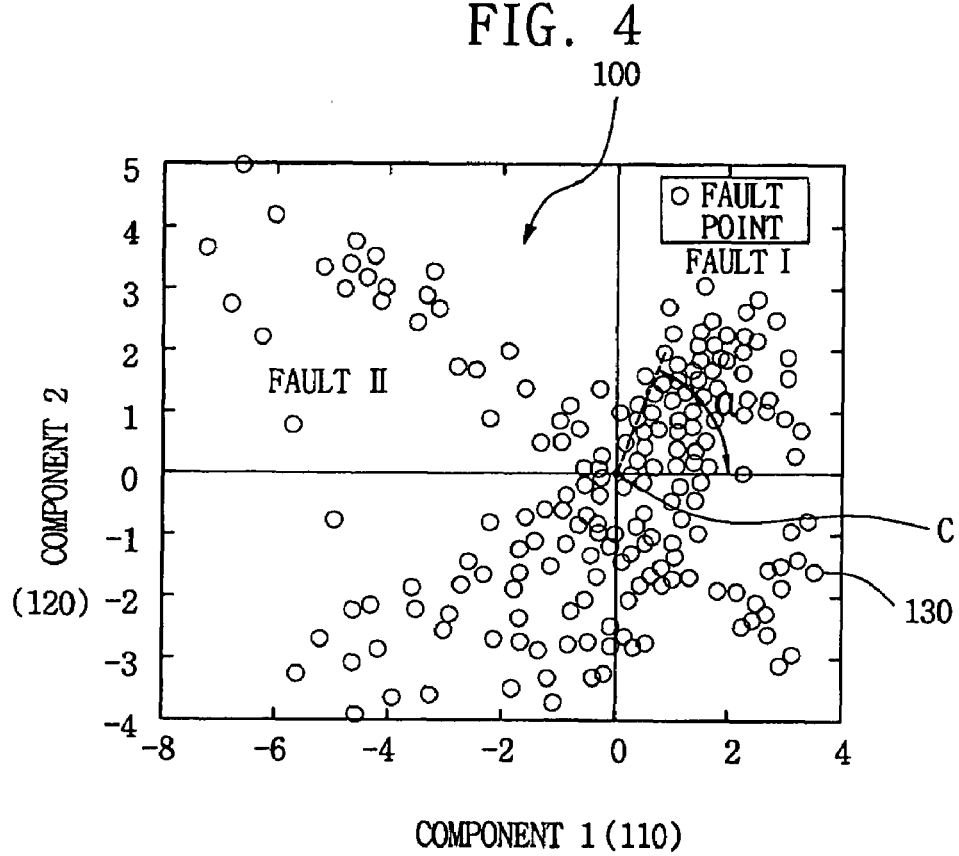
FIG. 4 is a graph illustrating first fault points in accordance with an example embodiment of the present invention.
Figure 5:
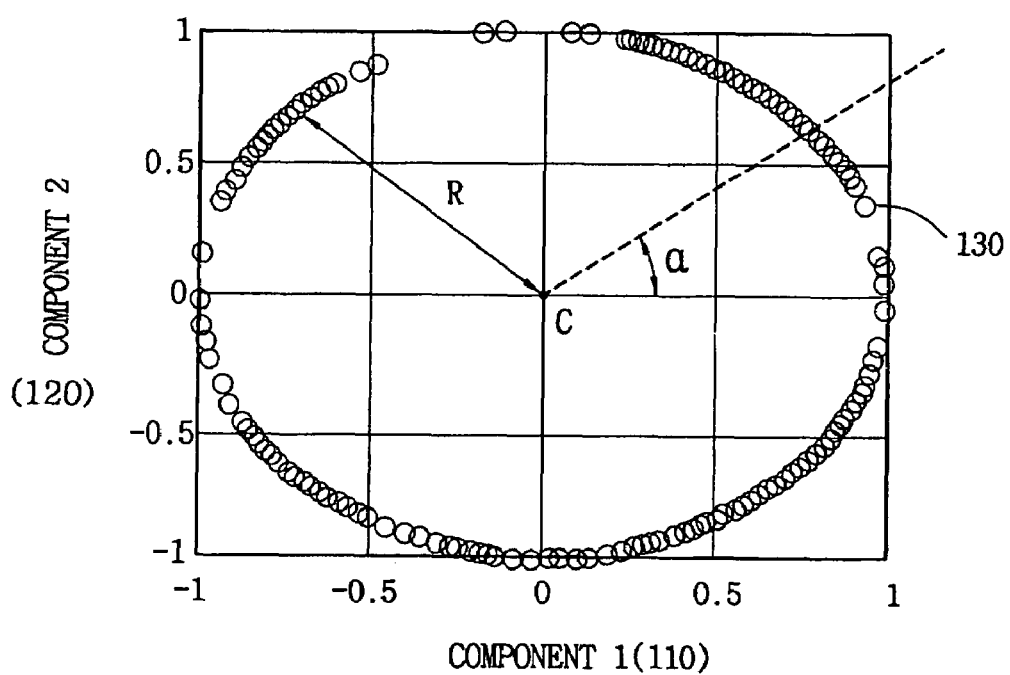
FIG. 5 is a graph showing the first fault points distributed to have the same radius according to angles in accordance with an example embodiment of the present invention.
Figure 6:
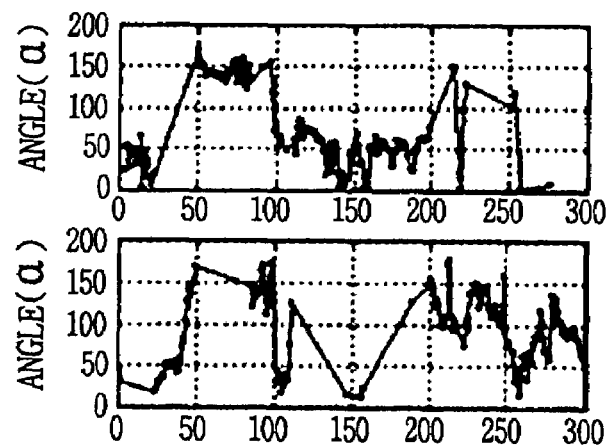
FIG. 6 is graphs illustrating angular distribution of first fault points according to a fault pattern group in accordance with an example embodiment of the present invention.
Figure 7:
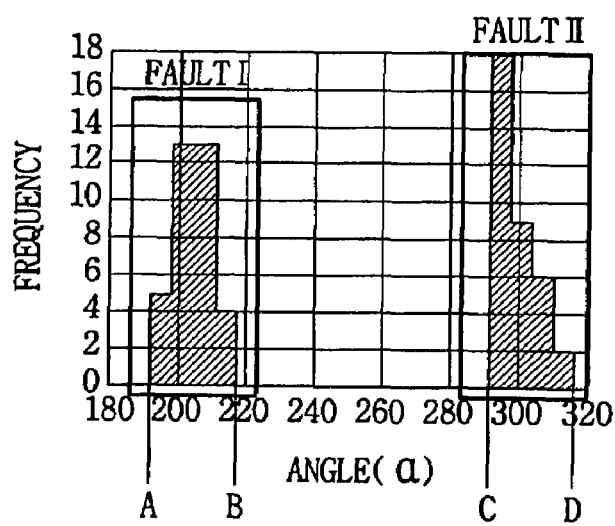
FIG. 7 is a graph of a group of fault points in accordance with an example embodiment of the present invention.

FIG. 2 is a flow chart illustrating a method of forming standard information to define fault patterns in accordance with an example embodiment of the present invention; FIG. 3 is a flow chart illustrating a method of determining a fault pattern of semiconductor manufacturing equipment in accordance with an example embodiment of the present invention; FIG. 4 is a graph showing first fault points distributed on a plane according to angles in accordance with an example embodiment of the present invention; FIG. 5 is a graph of first fault points distributed to have the same radius according to angles in accordance with an example embodiment of the present invention; FIG. 6 is graphs of angular distribution of first fault points according to a fault pattern group in accordance with an example embodiment of the present invention; and FIG. 7 is a graph of a group of fault points in accordance with an example embodiment of the present invention.

Hereinafter, a method of recognizing a fault pattern of semiconductor manufacturing equipment in accordance with example embodiments of the present invention will be described.

First, a standard information forming method will be described.

Referring to FIG. 2, operational data of semiconductor manufacturing equipment may be stored to a database (S100). The operational data may be used as standard (reference) data. Further details of the reference data will be provide below.

The database may include operational history information of the semiconductor manufacturing equipment. The semiconductor manufacturing equipment may be equipment with a high fault rate.

The operational data of the semiconductor manufacturing equipment (S110) may be provided to a first plane 100. The first plane 100 may be disposed according to two components (factors). The components may be considered factors which affect the fault rate. As illustrated in FIG. 4, the first plane 100 may be composed of a two-dimensional plane, e.g., first coordinates may include a first component axis 110 and a second component axis 120. The first and second components 110 and 120 may be faults generated during an operation of semiconductor manufacturing equipment, for example, temperature error and valve leakage, respectively.

A first set of fault points 130 may be determined from the operational data of the semiconductor manufacturing equipment (S120). It may also be determined whether the first set of fault points 130 resulted from the first or second component 110 or 120. As can be seen in FIG. 4, the first set of fault points 130 may be distributed on the first plane 100 (S130). That is, the first set of fault points 130 may be initially classified. In addition, the first set of fault points 130 may be detected to have a statistical significance level between 95-99% from the first and second components 110 and 120.

The first set of fault points 130 may be classified and grouped in detail by an angle spectrum analysis method (S140).

As illustrated in FIG. 4, each of the first set of fault points 130 distributed on the first plane 100 may have an angle α inclined from the axes of the first or second component 110 or 120. The angles may range from 0° to 360°.

In addition, as illustrated in FIG. 5, the first set of fault points 130 having angles α may be distributed on an X-Y two-dimensional plane constituting two axes, e.g., the first and second components 110 and 120, to have the same radius R from a center C.

As illustrated in FIG. 6, frequency of the first set of fault points 130 according to the angles may be determined depending on initially classified fault state groups, e.g., type of fault.

In addition, as illustrated in FIG. 7, frequency of the first set of fault points 130 may be determined based on angles of the fault state groups. FIG. 7 is a histogram. The X-axis represents the angle α, and the Y-axis represents the frequency variable. Therefore, an angle range having high frequency of the first set of fault points 130 may be defined by a first region between A-B degrees and a second region between C-D degrees. That is, it will be appreciated that the first set of fault points 130 have a high frequency in the first and second regions.

Therefore, the first set of fault points 130 showing similar frequency rates in the first and second regions may be groups having a similar angle α on the first component 110. That is, the first set of fault points 130 having similar angles may have similar fault states, or similar variables, which may have caused the fault state.

As described above, the first set of fault points 130 having similar frequency rates in the first and second regions may be classified into a first fault pattern group FAULT I and a second fault pattern group FAULT II, respectively.

Figures 8, 9:
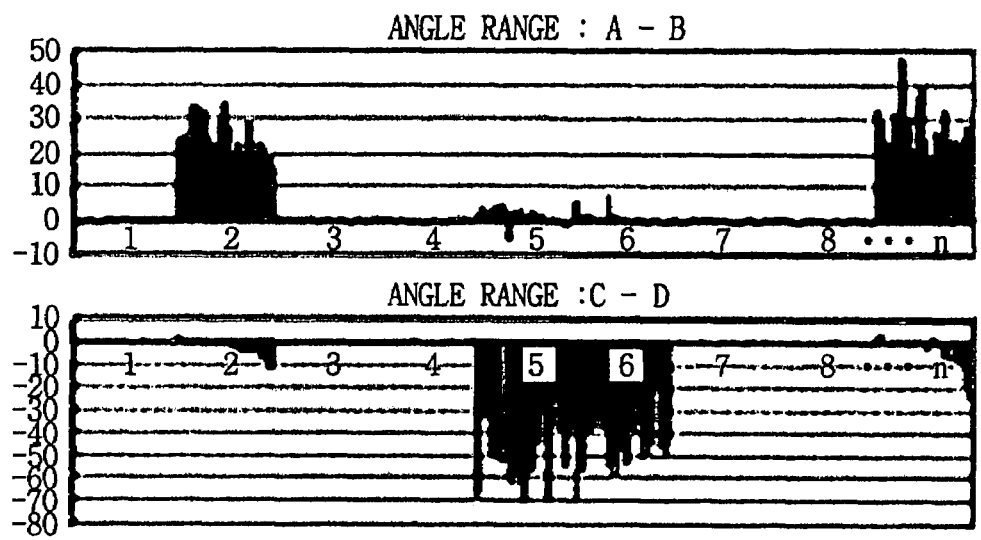
FIG. 8 is a graph of frequency depending on variables of first and second fault pattern groups illustrated in FIG. 5.
FIG. 9 is a table illustrating treatment information stored in a database in accordance with an example embodiment of the present invention.

Then, as illustrated in FIG. 8, it may be possible to determine contributions of the variables grouped into the first and second fault pattern groups FAULT I and FAULT II, which may be detected in a specific angle range, re-classified, and grouped (S150).

FIG. 8 is a graph illustrating frequency depending on variables of first and second fault pattern groups illustrated in FIG. 5, and FIG. 9 is a blank table illustrating treatment information stored in a database in accordance with an example embodiment of the present invention.

As illustrated in FIG. 8, the first fault pattern group FAULT I (angle range A-B) may have been mainly affected by a second variable and an nth variable, and the second fault pattern group FAULT II (angle range C-D) may have been mainly affected by a fifth variable and a sixth variable. The variables may be predetermined and known.

A first representative value may be extracted from variables that may have mainly affected the first and second pattern groups FAULT I and FAULT II. The first representative value may be obtained by calculating an average value or a median value of variables that may have mainly affected the first and second pattern groups FAULT I and FAULT II. The extracted first representative values may be defined as standard fault patterns representing each of the fault pattern groups FAULT I and FAULT II (S160). That is, the first fault pattern group FAULT I may be represented as a first standard fault pattern, and the second fault pattern group FAULT II may be represented as a second standard fault pattern. The first and second standard fault patterns may be referred to as major fault patterns, and may be subsequently used as reference fault patterns.

Therefore, the first fault pattern group FAULT I may have a first representative value, and the second fault pattern group FAULT II may have a first prime representative value.

Then, treatment information of the standard fault patterns having the first and first prime representative values is stored in the database (S170). "Treatment" may mean methods of correcting the faults.

As illustrated in FIG. 9, the treatment information may be information, for example, fault pattern recognition information, a standard fault pattern, an angle spectrum region (angle region), fault pattern characteristics, degree of danger, treatment, frequency, etc., according to the fault pattern groups FAULT I and FAULT II.

For example, if the first representative value of a variable contributing to the first fault pattern group FAULT I is a valve leakage, the fault pattern recognition information may be the first and second components 110 and 120 of the first fault pattern group FAULT I. In addition, information such as angle region A-B of the first fault pattern group FAULT I, a first standard fault pattern having the first representative value as valve leakage, degree of danger due to the valve leakage, treatment (e.g., how to correct the valve leakage) frequency of the valve leakage, etc., may be stored in the database.

As described above, the respective representative values and treatment information thereof according to the first and second fault pattern groups FAULT I and FAULT II may be stored in the database.

The descriptions above describe how the standard fault pattern for determining the fault pattern groups FAULT I and FAULT II may be defined from previous operational data of semiconductor manufacturing equipment, and treatment information for solving the standard fault pattern may be stored to the database. The treatment information and treatment operation are respectively generated and performed by the operator.

Hereinafter, a method of determining whether a fault pattern generated from a current operating semiconductor manufacturing equipment matches standard fault patterns stored in a database, and transmitting (e.g., displaying) treatment information thereof.

Referring to FIG. 3, standard information forming steps of providing fault patterns through an angle spectrum analysis may be performed. The information forming steps may be the same as described above with respect to FIG. 2.

The information forming method may include an equipment fault pattern detection step of providing patterns of a second set of fault points (not shown) detected from semiconductor manufacturing equipment through another angle spectrum analysis (i.e., second angle spectrum analysis), a step of comparing the detected semiconductor manufacturing equipment fault patterns with the standard fault pattern, and a step of determining whether the semiconductor manufacturing equipment fault pattern matches the standard information, and providing (displaying, printing, etc.) treatment information of the reference fault pattern.

The information forming method will be described in detail below.

Referring to FIG. 3, a second set of fault points may be detected from data transmitted from semiconductor manufacturing equipment (S200). The second set of fault points may be initially classified. A second plane (not shown) may be provided (S210). The second plane may include first and second components (not shown) to form an X-Y two-dimensional space. The first and second components (factors) have an affect on the second set of fault points.

In addition, the second set of fault points may be detected in the statistical confidence interval (S220).

The second set of fault points may be distributed on the second plane (S230).

Then, the second set of fault points may be classified in detail. Specifically, an angle α of each of the second set of fault points may be calculated with reference to any one axis of the first and second principal components. In addition, contributions of the variables with respect to the second set of fault points may be determined according to the angle α. Therefore, the second set of fault points may be grouped based on the contributions of the variables (S240). That is, the second set of fault points may be classified into a plurality of fault pattern groups FAULT I and FAULT II. The fault pattern groups FAULT I and FAULT II may have specific angle regions, respectively. Although in the example embodiment, the fault pattern groups are described as having FAULT I and FAULT II, similar with respect to FIG. 2, the fault patterns may be classified to have more then or less than two (2) FAULTS depending on the type of the second set of fault points.

Results of the second angle spectrum analysis method may match some of the first angle spectrum analysis results.

As described above, the second set of fault points detected from the semiconductor manufacturing equipment may be grouped to determine whether any of the groups match information of the first representative value included in the standard (stored) fault pattern (S250). For clarification purposes, the fault pattern group determined in step (S240) will be labeled "current" fault pattern group to distinguish from the fault pattern groups (reference) determined with respect for FIG. 2.

Referring to FIG. 3, when the current fault pattern group matches any of reference information provided in the database, treatment information of the reference fault pattern having the reference information may be displayed on a display screen. The treatment information may be transmitted to an operator (S251), and the operator may take any appropriate action including notifying a person in charge.

For example, when the current fault pattern group includes the first representative value of the first fault pattern group FAULT I as shown in FIG. 7, a second representative value of the current fault pattern group may be the same as the first representative value of the first fault pattern group FAULT I.

Then, the treatment information of the first fault pattern group FAULT I may be displayed. Therefore, the treatment information may be visually recognized by an operator, and the operator may instantly perform the proper treatment (corrective action).

On the other hand, when the current fault pattern does not match the standard information, a display may display the contributions according to variables, which may have caused the current fault pattern groups. Therefore, the operator receives the contributions according to the variables. That is, the contributions of the variables, which may have affected the current fault pattern groups FAULT I and FAULT II, may be determined. A second representative value, which may have mainly affected the fault pattern groups FAULT I and FAULT II, may be extracted from the determined contributions of the variables. In this process, the current fault pattern may be one or more variables, and the variables may be a fault pattern.

Further, the second representative value of the current fault pattern group may be determined as a new fault pattern (S252). The new fault pattern may be stored in the database. In addition, treatment information for the new fault pattern may also be stored in the database (S253).

Similar to the table shown in FIG. 9, the new treatment information may be, for example, new fault pattern recognition information, a standard fault pattern, an angle spectrum region (angle region), a standard fault pattern, degree of danger, new treatment, frequency, and so on, according to the fault pattern groups FAULT I and FAULT II. The new treatment information may be the same as a list of treatment information stored in the database for the previously stored operational data.

Therefore, the new fault patterns stored in the database may be used as the standard (reference) fault pattern during a subsequent manufacturing process.

As may be understood from the foregoing, it may be possible to store information of a plurality of fault patterns and treatment information to correct the fault patterns in a database on the basis of data from previously operated semiconductor manufacturing equipment. Therefore, it may be possible to rapidly correct a fault state often recurring in semiconductor manufacturing equipment and prevent the fault state from recurring.

In addition, it may possible to store a new fault state and treatment information thereof in a database in real time and on-the-fly without taking the semiconductor manufacturing equipment offline, when the new fault state is generated from semiconductor manufacturing equipment, thereby reducing time loss for updating the fault state.

Further, it may be possible to form standard fault patterns by performing angle spectrum analysis for a plurality of fault points detected from semiconductor manufacturing equipment during a process of determining a fault state, and directly match the standard fault patterns with semiconductor manufacturing equipment fault pattern detected from semiconductor manufacturing equipment, thereby simplifying a fault state pattern matching process.

While example embodiments of the present invention may have been described in connection with what may be considered to be the most practical and preferred example embodiments, it may be understood that the example embodiments may not limited to what have been disclosed, but on the contrary, it may be intended to cover various modification within example embodiments of the present invention.

What is claimed is:

1. A method of forming a reference fault pattern, comprising:
    performing an angle spectrum analysis by re-classifying fault points distributed on a plane, the plane including a first component axis and a second component axis, and the re-classifying fault points including calculating an angle for each of the fault points with reference to any one of the first component axis and the second component axis of the plane; and
    forming a reference fault pattern for defining a fault pattern of the re-classified fault points.

2. The method according to claim 1, wherein the angle spectrum analysis further comprises:
    distributing the fault points having the calculated angles on coordinates to have the same radius; and
    calculating frequency of each of the fault points according to the calculated angle to re-classify the fault points.

3. The method according to claim 1, wherein forming the reference fault pattern comprises:
    determining contributions of variables on the re-classified fault points;
    extracting one of the variables as a representative value; and
    setting the reference fault pattern having the representative value.

4. The method of claim 3, further comprising:
    storing the plane according to the re-classified points, the reference fault pattern, the representative value, and information to treat the reference fault patterns.

5. The method of claim 4, wherein the treatment information includes at least one of fault pattern recognition information, the reference fault pattern, an angle spectrum region, fault pattern characteristics, degree of danger, treatment, and frequency.

6. A method of monitoring equipment, comprising:
    determining a fault pattern for a first set fault points generated by monitored equipment, the determining step including performing a first angle spectrum analysis by re-classifying the first set of fault points distributed on a plane, the plane including a first component axis and a second component axis, and the re-classifying of the first set of fault points including calculating an angle for each of the first set of fault points with reference to any one of the first component axis and the second component axis of the plane;
    comparing the monitored equipment fault pattern with a reference fault pattern; and
    transmitting results of the comparison.

7. The method of claim 6, further comprising determining the reference pattern comprising:
    performing a second angle spectrum analysis by re-classifying a second set of fault points distributed on a plane, the plane including a first component axis and a second component axis, and the re-classifying second set of fault points including calculating an angle for each of the second set of fault points with reference to any one of the first component axis and the second component axis of the plane.

8. The method according to claim 7, wherein forming the reference fault pattern comprises:
    determining contributions of variables on the re-classified fault points;
    extracting one of the variables as a representative value; and
    setting the reference fault pattern having the representative value.

9. The method of claim 7, further comprising:
    storing the reference fault pattern and storing at least one of treatment information for the reference fault pattern, fault pattern recognition information, an angle spectrum region, fault pattern characteristics, degree of danger, and frequency of the fault pattern.

10. The method according to claim 9, further comprising:
    performing a treatment action if the monitored equipment fault pattern matches the stored reference fault pattern.

11. The method according to claim 6, wherein the first angle spectrum analysis comprises:
    calculating angles for each of the first set of fault points;
    distributing the first set of fault points having the calculated angles on coordinates to have the same radius; and
    calculating frequency of each of the first set of fault points according to the calculated angle to re-classify the fault points.

12. The method according to claim 6, wherein the first angle spectrum analysis step further comprises:
    calculating angles for each of the first set of fault points;
    distributing the first fault points having the calculated angles on coordinates to have the same radius; and
    calculating frequency of each of the first set of fault points according to the calculated angle to re-classify the fault points.

13. The method according to claim 12, wherein the step of determining the fault pattern for the first set of fault points further comprises:
    determining contributions of variables on the re-classified fault points;
    extracting one of the variables as a representative value; and
    setting the reference fault pattern having the representative value.

14. A method of monitoring equipment, comprising:
    performing a first angle spectrum analysis on a first set of fault points generated by an equipment;
    determining a reference fault pattern for the first set fault points by determining contributions of variables to the first set of fault points;
    storing the reference fault pattern to a database;
    performing a second angle spectrum analysis of a second set of fault points generated by the monitored equipment;
    determining a fault pattern for the second set fault points generated by determining contributions of variables to the first set of fault points;
    comparing the fault pattern with the stored reference fault pattern; and transmitting at least one of
- treatment information if the fault pattern matches the stored reference fault pattern and
- variables affecting the fault pattern if the monitored equipment fault pattern does not match the reference fault pattern.

15. The method according to claim 14, wherein the first angle spectrum analysis comprises:
- calculating an angle for each of the first set of fault points distributed on a first plane;
- distributing the first set of fault points to have the same radius; and
- calculating frequency of the first set of fault points to re-classify the first set of fault points.

16. The method according to claim 15, wherein forming the reference fault pattern comprises:
- determining contributions of the variables, the variables effecting faults of the re-classified first set of fault points;
- extracting from the variables a high fault variable to determine a first representative value; and
- setting the reference fault pattern having the first representative value.

17. The method according to claim 14, wherein the second angle spectrum analysis step comprises:
- calculating an angle for each of the second set of fault points distributed on a first plane;
- distributing the second set of fault points to have the same radius; and
- calculating frequency of the second set of fault points to re-classify the second set of fault points.

18. The method according to claim 17, wherein determining the fault pattern for the second set of fault points comprises:
- determining contributions of variables, the variables effecting faults of the re-classified second set of fault points;
- extracting from the variables a high fault variable to determine a first representative value; and
- setting the fault pattern having the first representative value.

19. The method of claim 14, wherein if the fault pattern does not match the reference fault pattern:
- storing the fault pattern as a new reference fault pattern to the database.

20. The method of claim 19, wherein the determination of the new fault pattern and the storing of the new fault pattern are accomplished on-the-fly.

* * * * *